United States Patent [19]

Markowitz

[11] 4,343,311
[45] Aug. 10, 1982

[54] ATRIAL REFRACTORY CONTROL FOR R-WAVE REJECTION IN PACEMAKERS

[75] Inventor: H. Toby Markowitz, Anoka, Minn.

[73] Assignee: Medtronic, Inc., Minneapolis, Minn.

[21] Appl. No.: 145,052

[22] Filed: Apr. 30, 1980

[51] Int. Cl.³ .............................................. A61N 1/36
[52] U.S. Cl. ............................................. 128/419 PG
[58] Field of Search ................................. 128/419 PG

[56]     References Cited
        U.S. PATENT DOCUMENTS

| 3,903,897 | 9/1975 | Woollons et al. | |
| 4,043,347 | 8/1977 | Renirie | 128/419 PG |
| 4,059,116 | 11/1977 | Adams | 128/419 PG |
| 4,091,817 | 5/1978 | Thaler . | |

FOREIGN PATENT DOCUMENTS 2701104  7/1978  Fed. Rep. of Germany .

OTHER PUBLICATIONS

Fischler et al., "IEEE Transactions on Bio-Medical Engineering", vol. 16, No. 1, Jan. 1969, pp. 64–68.

Primary Examiner—William E. Kamm
Attorney, Agent, or Firm—Merchant, Gould, Smith, Edell, Welter & Schmidt

[57] ABSTRACT

An artificial heart pacemaker and control circuit having an atrial synchronous pacing mode includes an output pulse generator for delivering stimulating pulses to the ventricle of the heart, and atrial and ventricular sensing amplifiers for detecting, respectively, atrial and ventricular contractions. The atrial sense amplifier starts an A-V delay timer which provides a delayed triggering pulse to the pulse generator to maintain A-V synchrony. Circuitry is provided for blanking or turning off the atrial sensing amplifier during the time that the ventricular sensing amplifier is refractory, and preferably for a short time interval thereafter, to prevent delivery of an output pulse in response to a premature ventricular contraction erroneously sensed as an atrial contraction.

8 Claims, 4 Drawing Figures

ATRIAL REFRACTORY CONTROL FOR R-WAVE REJECTION IN PACEMAKERS

TECHNICAL FIELD OF THE INVENTION

This invention pertains generally to the field of electrical heart pacemakers, and more specifically to improvements in control circuits for atrial synchronous pacemakers or other pacemakers capable of operating in an atrial synchronous mode.

BACKGROUND OF THE PRIOR ART

Atrial synchronous pacemakers are designed for use on patients whose hearts have normal atrial self pacing, but, due to a defect in the conduction from the atrium to the ventricle, the ventricles fail to beat or keep pace with the atrial rhythm. Atrial synchronous pacemakers are designed to sense the naturally occurring atrial contractions (depolarizations) and, at the end of a short time interval, to provide an electrical stimulation pulse to the ventricles of the heart so as to induce a ventricular contraction. The time delay interval is selected so that the atrial and ventricular contractions are synchronized with an appropriate delay interval for efficient pumping. Atrial synchronous pacing attempts to take the place of missing natural conduction of stimulating pulses from the atrium to the ventricle in the heart, while the heartbeat rate is free to follow, within limits, the natural rhythm established by the atrial self-pacing of the patient. Often other features are combined with atrial synchronous pacing, such as an upper rate limit, or reversion to fixed rate pacing if the spontaneous atrial rate drops below a predetermined rate. Also, provisions may be provided as is known in the art for programming the pacemaker after implantation to adjust the atrial-ventricular delay, upper or lower rates, and other operating parameters. A ventricular inhibit function can also be provided so that if a ventricular depolarization does follow in response to an atrial depolarization, the ventricular depolarization will be sensed and the pacemaker will be inhibited from delivering a competitive ventricular stimulating pulse. In that manner, the stimulating pulses are delivered only if needed.

In addition to atrial synchronous pacemakers, other types of pacemakers capable of operating in a number of modes include atrial synchronous operation as one possible mode of operation. Dual sense/dual pace atrial-ventricular pacemakers, sometimes referred to as fully automatic pacemakers, are capable of selectively delivering stimulating pulses to both the atrium and the ventricle, and are also capable of sensing beats occurring in both chambers and operating as appropriate to maintain A-V synchrony. That type of fully automatic pacemaker will operate in an atrial synchronous mode if the patient's atrium is self pacing above the minimum rate (thus inhibiting delivery of atrial stimulation pulses) and if the ventricles are not contracting on their own at the proper time interval following an atrial contraction. In that case, a ventricular stimulation pulse will be delivered at the selected A-V delay interval following the atrial contraction, thus resulting in atrial synchronous operation.

Pacemakers operating in an atrial synchronous mode are subject to certain errors which, under certain circumstances, can lead to the delivery of a ventricular stimulation pulse at an inappropriate and possibly dangerous time period of the heartbeat cycle. The problem can occur when a premature ventricular contraction occurs prior to an atrial contraction. Although the atrial sense amplifier is intended to respond only to atrial depolarizations (P-waves) of the electrogram, in fact the R-waves from a ventricular depolarization may be sensed as a P-wave by the atrial sense amplifier. This starts the A-V delay interval, following which the pacemaker delivers a ventricular electrical stimulation pulse. This pulse may fall in time in the vulnerable period of the heart during repolarization from the premature ventricular contraction. Delivery of a stimulation pulse during this vulnerable period is medically unsound, because it could be dangerous to the patient under some circumstances, as it might cause fibrillation of the heart.

It has been recognized in the prior art that the above sequence of events beginning with a premature ventricular contraction and leading to delivery of a ventricular stimulation pulse during the vulnerable period is unacceptable, and various solutions have been proposed. Drug therapy has been used in conjunction with atrial-triggered synchronous ventricular pacemakers in an attempt to suppress premature ventricular contractions so that they would not be detected by the atrial sensing circuit. However, drug therapy has limitations and may be ineffective or inappropriate in certain circumstances and for certain patients. Electronic filtering has also been used in conjunction with the atrial sensing amplifier in order to discriminate the P-wave from the R-wave so as to reject the latter. However, filtration by itself is not workable or reliable in discriminating atrial from ventricular events, because of the inherent variabilities of the shape and frequency composition of R-waves and P-waves in man. The R-wave in some individuals is more like the P-wave in other individuals, thus greatly complicating any attempt at discrimination by electronic filtering.

The present invention overcomes the above noted problem by sensing both in the atrium and ventricle and by using timing considerations to discriminate between P-waves and R-waves so that a stimulating ventricular pulse is delivered only in response to an actual atrial contraction, and not in response to a premature ventricular contraction, when operating in atrial synchronous mode.

The invention is useful in both unipolar and bipolar pacemakers, and is particularly useful in unipolar pacemakers, because in the prior art it has been more difficult to discriminate P-waves from R-waves in the case of unipolar pacemakers. The preferred embodiment shown herein is for a unipolar pacemaker.

SUMMARY OF THE INVENTION

According to the present invention there is provided a pacemaker and a control circuit for use therein for selectively delivering stimulating pulses to the heart in an atrial synchronous mode of operation, including terminals for connection both to the ventricle and atrium of the patient's heart. Generating means are provided for selectively delivering ventricular electrical stimulation pulses through the ventricular terminal to the ventricle of the heart. A ventricular sense amplifier connects from the ventricular terminal and is operative for sensing ventricular beats of the heart. The ventricular sense amplifier has an insensitive or refractory period following the sensing of a ventricular heartbeat or the occurrence of a stimulation pulse. An atrial sense amplifier is connected to the atrial terminal for sensing P-waves indicative of atrial depolarizations, and delay means operatively connected to the atrial sense amplifier operate to trigger the generation of a ventricular electrical stimulating pulse after a predetermined time interval following a sensed atrial depolarization. Control means are operatively associated with the atrial sensing amplifier to render it inoperative during the refractory period of the ventricular sense amplifier, so that premature ventricular contractions or other ventricular events will not be erroneously detected by the atrial sense amplifier.

According to another aspect of the present invention, the atrial sensing amplifier is retained in its inoperative condition during the refractory period of the ventricular sense amplifier and also for a predetermined time interval thereafter, so as to avoid detection of ventricular events delayed by the propagation time thereof from a low point in the ventricle to the atrial lead in the heart.

DETAILED DESCRIPTION OF THE PREFERRED EMBODIMENT

Figure 1:
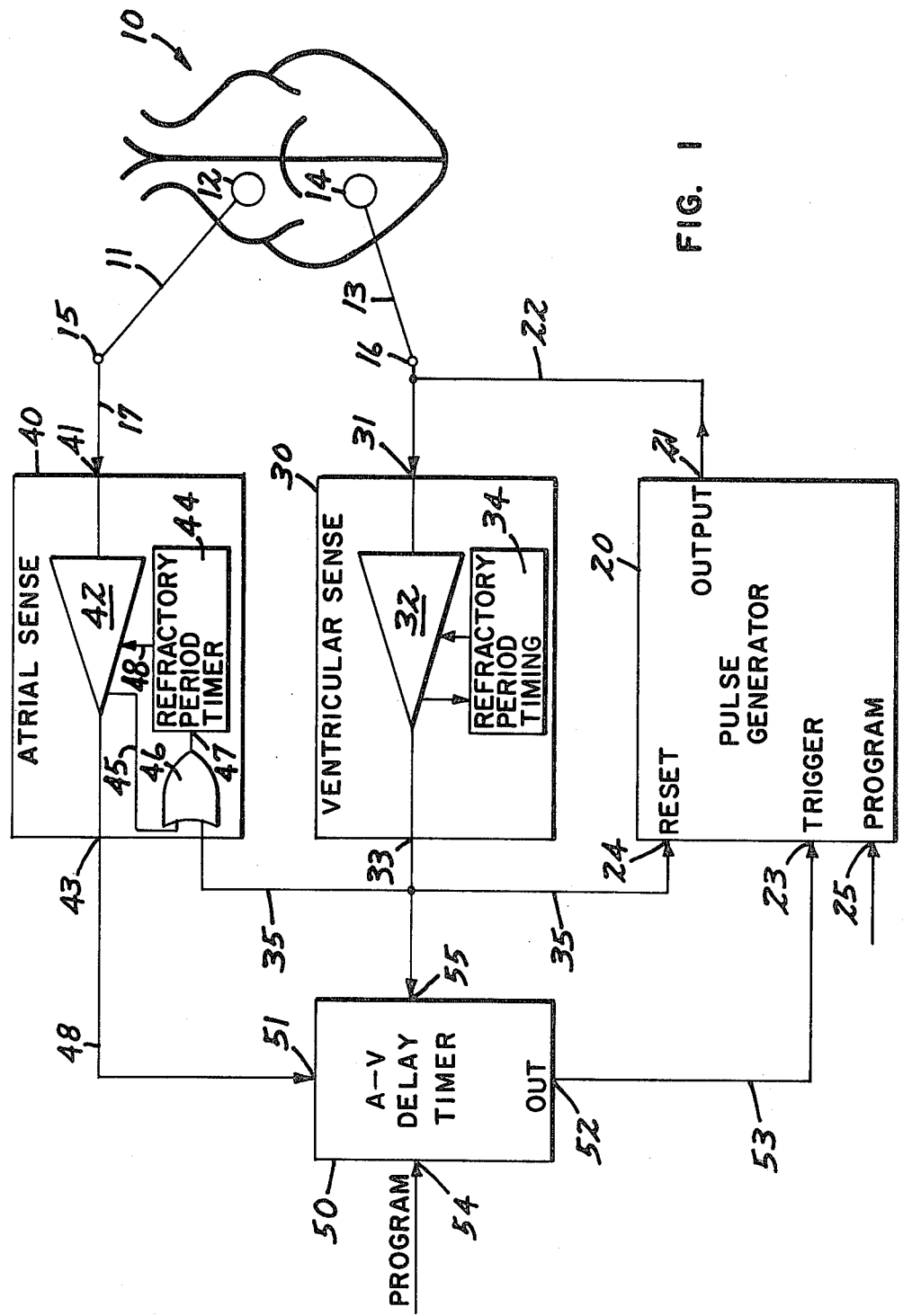
FIG. 1 is a block diagram of a heart pacemaker according to the present invention.

In FIG. 1, the major functional elements of a pacemaker incorporating the present invention are shown in block diagram form. The pacemaker could either be external or implantable, but in either case it is connected through leads to the patient's heart. Reference number 10 indicates a diagrammatic representation of the patient's heart. A lead 11 extends to the atrium or upper chamber of the heart, and lead 11 has an electrode 12 which contacts the heart at the atrium. Similarly, lead 13 extends to the ventricle or lower chamber of the heart, and it has an electrode 14 at its end which attaches to the heart at the ventricle. Although two separate leads 11 and 13 are shown, a single multiple conductor lead having separate electrodes at its tip and at a point along its side may be used for contact with the ventricle and atrium, as is generally known in the art. Leads 11 and 13 connect respectively to terminals 15 and 16 provided on the housing of the pacemaker, for connection to the various electrical components and circuits within the pacemaker.

Within the pacemaker, a pulse generating circuit 20 is provided. Generator 20 functions to selectively produce electrical heart stimulation pulses at its output 21, which connects through conductor 22 to terminal 16 so that the generated output pulses will be conducted to the ventricle of the heart. When operating in atrial synchronous mode, pulse generator 20 develops an output pulse in response to an input signal at its trigger input 23. Pulse generator 20 preferably also has a backup mode to pace the heart at a minimum rate in the event that no triggering pulses are received, or in the event the triggering pulses occur at below the minimum rate. In any event, the pulse generator 20 will be inhibited from delivering an output pulse when a reset pulse is applied at its reset input 24. Specific circuits suitable for the functions of pulse generator 20 described above are generally known in the art and are not set forth in detail. Also as generally known in the art, the minimum rate at which switching to the backup mode occurs may be adjusted by a program input 25 from an r.f. program device as is known in the art.

A branch of conductor 22 connects to input 31 of the ventricular sensing circuit 30. Sensing circuit 30 contains amplifying and filtering circuits, indicated by reference number 32, as are generally known in the art for detecting the ventricular depolarization (QRS complex) of the electrogram from the patient's heart indicative of a ventricular contraction. When a ventricular contraction is detected, a signal indicative thereof is provided at output 33 of ventricular sensing circuit 30. Sense amplifiers used in pacemakers generally experience a period of insensitivity for a certain time interval following either the detection of the heart contraction, or the application of the generated stimulating pulse. During this insensitive period, referred to as the refractory period, the amplifier is temporarily "off" or otherwise insensitive to whatever signals may be applied to its input. The refractoriness is useful in that it renders the sense amplifier insensitive to "ringing" or rapid pulse triggerings which might occur immediately following a contraction and which, if sensed and amplified, might give unnecessary or misinformative inputs to the pacemaker logic circuits. To an extent the refractoriness following an input signal may be inherent in the specific electronic design of the filter and amplifier, due to choice of components and usually extremely low current biasing conditions, so that an input signal momentarily disrupts the quiescent point rendering the circuit insensitive for a given recovery time. Alternatively, a specific timing or blanking circuit can be provided in conjunction with the sense amplifier or filters to render the sensing circuit refractory for a specifically selected time interval following detection of a ventricular event. In FIG. 1, Reference number 34 refers to the refractory period timing, but it will be understood that this may either be a separate timing circuit, as suggested in the drawing, or it may well be simply an insensitive period inherent in the design of the sensing amplifier and filtering circuits. The manner of characterizing the refractory period timing by a separate block in FIG. 1 should not be construed to be limited only to separate timing means for the refractory period.

An atrial sensing circuit 40 is provided, having an input 41 which connects via conductor 17 to atrial terminal 15. Atrial sense circuit 40 includes amplifying and filtering circuits indicated by reference number 42 which operate to provide an output at terminal 43 in response to the detection of the P-wave portion of the electrocardiogram of the heart indicating an atrial contraction. As previously mentioned, although filtering circuits may be provided in an attempt to distinguish the P-wave from the R-wave, such filtering is not always reliable due to variations in the nature of the P and R-waves from patient to patient.

The amplifier and filtering circuits 42 of the atrial sense amplifier may be of conventional design as generally known in the art, except that according to the present invention a particular refractory or insensitive period for the atrial sensing circuit is provided. Although the atrial refractory period can be controlled by selection of the components and operating points for the electronic components of the sense amplifier, in the preferred embodiment a separate refractory period timing control 44 is provided. This may take the form of a digital timer, or an analog timing circuit such as a one shot multivibrator or equivalent. Upon detection of a signal by the sense amplifier and filtering circuits 42, an output signal indicative thereof is provided at output 43. At the same time a signal is provided through conductor 45 and OR gate 46 to input 47 of refractory period timer 44. Timer 44 then controls amplifier and filtering circuits 42 via control line 48 to render them insensitive to input signals for the duration of the refractory period while timer 44 is timing out. This may be accomplished through a suitable gate, switching or clamping circuit within or attached to the sensing amplifier or input circuits.

Another input is provided to OR gate 46 for rendering the atrial sensing circuit 40 refractory, and that input is provided by a branch of conductor 35 which connects from the output 33 of the ventricular sensing circuit 30. The function of this connection is to ensure that the atrial sensing circuits are off or refractory at the same time as the ventricular sensing circuits, to enable discrimination between atrial and ventricular events as explained in greater detail below.

Output 43 of atrial sense circuit 40 connects via conductor 48 to input 51 of the A-V delay timer 50. Timer 50 may be a digital or analog timing circuit, and it functions to provide an output signal at its output 52 at a predetermined time interval following receipt of an input signal at its input 51. The output signal is conveyed over conductor 53 to the trigger input 23 of pulse generator 20. A-V delay timer 50 provides a time delay interval between atrial and ventricular contractions so that the ventricles can be filled before they are contracted. A typical A-V delay interval is approximately 120 milliseconds, and provisions may be provided as is generally known in the prior art for programming the timer at input 54 to select the delay interval. Timer 50 also has a reset input which connects to a branch of lead 35 so that a signal from ventricular sensing circuit 30 functions to reset or cancel an interval being timed out by timer 50.

In operation of the pacemaker of FIG. 1 in the atrial synchronous mode, the naturally occurring atrial contraction generates a depolarization (P-wave) which is picked up by electrode 12 and conveyed through lead 11, terminal 15 and conductor 17 to input 41 of the atrial sensing circuit 40. The P-wave is detected and amplified and causes an output at 43 which is conveyed to input 51 of the A-V delay timer 50. This starts the timing of an atrial-ventricular (A-V) delay interval. At the end of the A-V delay interval, an output signal at output 52 is conveyed to the trigger input 23 of pulse generator 20, causing it to deliver a ventricular output stimulating pulse to the heart via conductor 22, terminal 16, lead 13 and electrode 14. In the event of a naturally occurring ventricular contraction following the atrial contraction and occurring prior to the timing out of the A-V delay timer 50, such ventricular contraction will be detected by its depolarization (R-wave) conducted through lead 13, terminal 16 to input 31 of the ventricular sensing circuit 30. There the R-wave is detected and amplified and causes an output at 33 which is conveyed over conductor 35 to reset A-V delay timer 50 and pulse generator 20 so that no output pulse will be generated for that heartbeat cycle, since none is needed.

It is common to provide a backup mode for an atrial synchronous pacemaker. If the heartbeat rate drops below a preselected or programmed minimum rate, pulse generator 20 reverts to a mode in which it delivers ventricular stimulating pulses at a minimum heartbeat rate, subject to reset and inhibition in the event of detection of a naturally occurring ventricular contraction by ventricular sensing circuit 30.

An important feature of the present invention lies in the control of the refractory or insensitive periods of the atrial and ventricular sensing circuits. As previously mentioned, a ventricular event, either an R-wave or a stimulating pulse, causes the ventricular sensing circuit to go off or refractory for a certain period of time. Similarly, the detection of an event by the atrial sensing circuit 40 causes it to go off or refractory for a period of time. In the preferred embodiment, timer 44 controls the refractory period of the atrial sensing circuit, and the detection of an event by the atrial sense amplifier causes a control signal via lead 45 and OR gate 46 to start timer 44 and initiate the refractory period. Additionally, an output from ventricular sensing circuit 30 is coupled to the refractory period timer 44 for the atrial sensing circuit via conductor 35 which connects to an input of OR gate 46. Timer 44 is of the retriggerable type, so that an input signal at input 47 starts the time period, and if an additional input is received during the time period, timer 44 is reset to start its time-out over again. The connection of the ventricular sensing circuit to the atrial refractory period timer is for the purpose of ensuring that a ventricular event turns off the atrial sensing circuit. This is important in discriminating between P-waves and R-waves picked up by the atrial lead and appearing at the input of the atrial sense amplifier.

Because of the relatively great strength of electrical signals associated with ventricular events, it is likely that they would be detectable both on the atrial and ventricular leads. However, because the electrical P-wave signals associated with atrial contractions are relatively weak and localized, it is likely they would be detected only on the atrial lead. It might therefore be assumed that if a signal occurs both on the atrial and ventricular leads, it is of ventricular origin, while if it occurs only on the atrial lead, it is of atrial origin. However, that presumption assumes that both sense amplifiers operate continuously. Premature ventricular contractions might be detected only by the atrial amplifier if they occur during the refractory period of the ventricular amplifier, thus leading to the problem existing in the prior art discussed above.

The present invention solves this problem by maintaining certain operating conditions regarding the on or off condition of the sensing amplifiers. A first condition is that a ventricular event, either a natural ventricular contraction or a ventricular stimulation pulse, will cause both the atrial and ventricular sensing amplifiers to go to their off or refractory condition. A second condition is that the atrial sensing amplifier will be allowed to turn on only when the ventricular amplifier is known to be operating. Therefore, a premature ventricular contraction occurring during the refractory period of the ventricular sensing amplifier will not be erroneously detected by the atrial sensing amplifier as an atrial event, and consequently the danger of delivering a stimulating pulse during the vulnerable period of the heart as outlined above is avoided.

In the preferred embodiment, an output from the ventricular sensing amplifier is used to turn off the atrial sensing circuit by starting or resetting its refractory period timer 44. The time period for timer 44 is selected, in conjunction with the inherent refractory period of ventricular sensing circuit 30, or in conjunction with its specific refractory period timing circuit, if any, so that the atrial sensing amplifier is not returned to its on condition until the ventricular sensing amplifier is also returned to its on condition.

Figure 2A:
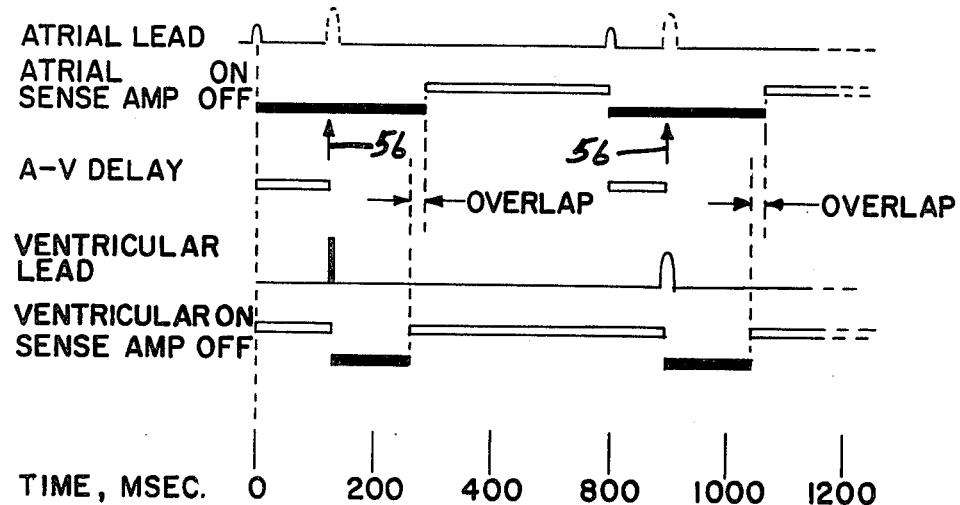
FIGS. 2A and 2B are graphs of pertinent waveforms showing the operation of the pacemaker of FIG. 1.

The timing relationships of the various signals and sensing periods are illustrated in the timing chart, FIG. 2A, which shows the signals appearing at the atrial and ventricular leads, and the conditions of the atrial and ventricular sense amplifiers and the A-V delay circuit of the pacemaker of FIG. 1, for a period of time through approximately two heartbeats. The horizontal axis represents time, starting at zero and running through approximately 1,200 milliseconds. For illustrative purposes, FIG. 2A shows two heartbeat cycles, both in atrial synchronous operation, but with the first resulting in the delivery of a stimulating pulse, and the second cycle showing the occurrence of a spontaneous ventricular contraction in the proper time interval following the atrial contraction.

At time zero, a P-wave occurs at the atrial lead. This has two effects: It starts the A-V time delay period and it renders the atrial sensing amplifier in its off or refractory condition. In the preferred embodiment the A-V delay is 120 milliseconds. At 120 ms, since no R-wave indicating a ventricular contraction has been received, the pulse generator delivers a stimulating pulse to the heart. As this occurs, it induces a corresponding signal in the atrial lead, but since the atrial sensing amplifier is off, the signal is not detected. In FIG. 2A, the effect of the ventricular stimulating pulse at the atrial lead is shown as a dotted line spike. At the same time that the ventricular pulse is delivered, it is of course sensed at the ventricular amplifier and the ventricular amplifier then goes into its refractory period. The ventricular sense amplifier also resets the refractory period timer 44 for the atrial sensing amplifiers, as indicated at reference number 56, restarting the atrial refractory period.

The atrial and ventricular sense amplifiers remain off following the ventricular stimulation pulse. At the end of approximately 140 ms, the ventricular sensing amplifier returns to its on condition, but the atrial sensing amplifier remains off for an additional 30 ms, or 170 ms from the time it was reset at the ventricular pulse. Thus, the atrial sensing amplifier is kept off in the preferred embodiment not only during the duration of the ventricular sense amplifier refractory period, but also for an additional 30 ms overlap for reasons explained further below with respect to FIG. 2B.

In FIG. 2A, after both the ventricular and atrial sense amplifiers return to their on condition, the pacemaker waits for the occurrence of the next signal from the heart. Assuming that the natural atrial pacing of the heart is operating normally, a P-wave is next detected at the atrial sensing amplifier, at approximately 800 ms in FIG. 2A. This again starts the A-V delay timer and turns off the atrial sensing amplifier. In this example, it is assumed that the normal conduction in the heart is working and a ventricular contraction takes place prior to the end of the A-V time delay period. The R-wave is shown on the ventricular lead line in FIG. 2A at about 900 ms, and it causes a resetting or termination of the A-V delay, an initiation of the ventricular sense amplifier refractory period, and a resetting of the atrial sense amplifier refractory period. After a further 140 ms, the ventricular sense amplifier returns to its on condition, and an additional 30 ms later the atrial sense amplifier returns to its on condition.

It will be apparent from a study of the circuit of FIG. 1 and the operating timing chart of FIG. 2A that the possibility of erroneously detecting a premature ventricular contraction (PVC) as an atrial contraction has been precluded: If it occurs during the off time of the sense amplifiers, it is simply ignored by the pacemaker, but if it occurs during the on time of the atrial sensing amplifier, it will according to the present invention also of necessity occur during the on time of the ventricular sensing amplifier. If a PVC does occur while the ventricular amplifier is on, regardless of whether the atrial amplifier is on, the A-V delay timer will be reset or cancelled, so that the stimulating pulse will not be delivered one A-V delay interval following the PVC.

Figure 2B:
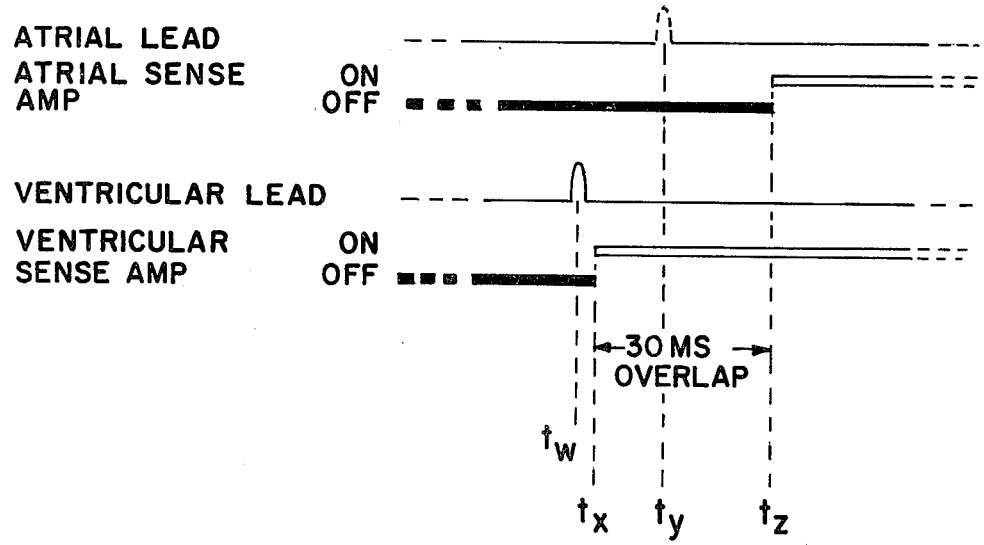

For the reasons pointed out above it is seen to be important that the atrial sense amplifier not be returned to on condition until the ventricular sense amplifier is also turned on. Further, it is preferable that the turn-on of the atrial sense amplifier should be delayed for a short interval after the turn-on of the ventricular sensing amplifier. This is seen further with the aid of FIG. 2B. In FIG. 2B, the atrial and ventricular lead signals and the on or off status of the atrial and ventricular sensing amplifiers are shown as in FIG. 2A. However, in FIG. 2B an expanded horizontal scale is used so that the 30 ms overlap time period between the turn-on of the ventricular sensing amplifier and the turn-on of the atrial sensing amplifier is more clearly seen. FIG. 2B thus only covers a portion of a heartbeat cycle, corresponding to approximately the 250 to 350 ms range following the sensing of a P-wave. For convenience four specific times have been labeled $t_w$ through $t_z$ for convenience in illustrating the purpose of the overlap. Time $t_x$ is the end of the ventricular refractory period, which in the preferred embodiment is 140 ms following a ventricular event. Time $t_z$ is the termination of the atrial sense amplifier refractory period, in the preferred embodiment 170 ms from the resetting of the atrial refractory period timer by a ventricular event.

Assume now that a PVC occurs at time $t_w$, just prior to the turn-on of the ventricular sense amplifier. Of course if the PVC occurred just after the turn-on of the ventricular sensing amplifier, the pulse generator and A-V delay timer would be reset as noted above, removing any possibility of an inappropriate response by the pacemaker. However, with the PVC occurring just prior to the ventricular sensing amplifier turn-on, the PVC will not result in a resetting action as noted above. If the atrial sensing amplifier were to be turned on simultaneously with the ventricular amplifier at time $t_x$, there would exist a possibility that a propagation delay in the PVC arriving at the atrial lead may result in the PVC being detected by the atrial amplifier and not the ventricular amplifier. For example, if a PVC originates in the low ventricle, there may be a short but significant time delay for the electrical signal generated by the PVC to propagate to the atrium where it would be picked up by the atrial lead and conducted to the atrial sense amplifier. If both amplifiers were turned on simultaneously, a PVC occurring just before turn-on mighht be detected by the atrial lead alone, with the result that it would be interpreted as an atrial event, thus triggering the A-V delay timer and the pulse generator one A-V time delay interval later. Of course, such a situation might produce a stimulating pulse during the vulnerable period of the heart following the originating PVC.

To avoid this possibility, in the preferred embodiment the atrial sensing circuit is maintained in its off condition for a particular time period, referred to as the overlap, beyond the refractory period of the ventricular sensing circuit. In the preferred embodiment this overlap is 30 ms, so that the atrial sensing circuit does not turn on until time $t_z$ in FIG. 2B. Thus, the propagation-delayed PVC occurring at the atrial lead at time $t_y$ still falls in the refractory or off time period of the atrial sensing amplifier and is thus ignored. The 30 ms time interval is chosen to provide adequate safety margin to protect against the above noted occurrence while still being short enough not to interfere with maximum pacing rate considerations for the pacemaker.

Figure 3:
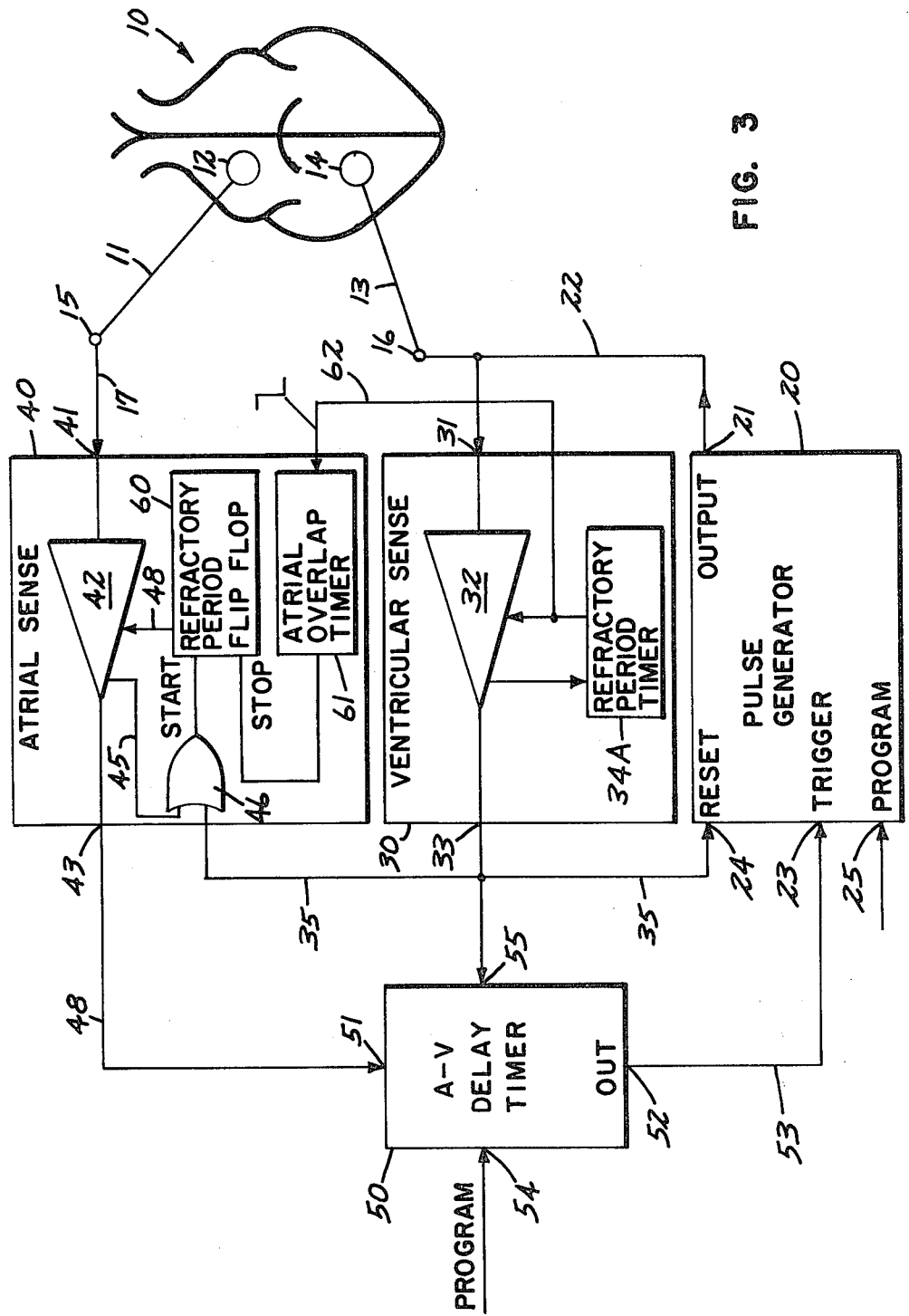
FIG. 3 is a block diagram, similar to FIG. 1, of an alternate embodiment of a pacemaker according to the present invention.

Referring to FIG. 3, an alternate embodiment of a heart pacemaker according to the present invention is shown. The embodiment of FIG. 3 is similar in many respects to the embodiment of FIG. 1, and like reference numbers are used for the corresponding elements in FIGS. 1 and 3. The main difference of FIG. 3 compared with FIG. 1 is the use of refractory period flip-flop 60 and atrial overlap timer 61, instead of the refractory period timer 44 of FIG. 1.

Specifically, OR gate 46, whose inputs are connected as in FIG. 1, has its output connected to one input of refractory period flip-flop 60. This input is labelled "start" in FIG. 3. The other input to flip-flop 60, labelled "stop", in FIG. 3, connects from the output of atrial overlap timer 61. Conductor 48 connects from flip-flop 60 to control the blanking or refractory period of the atrial sensing amplifier 42.

The input to atrial overlap timer 61 is provided over lead 62 from refractory period timer 34A. In the embodiment of FIG. 3, refractory period timer 34A is a specific timing circuit that controls the refractory period of ventricular sense amplifier 32. When amplifier 32 detects a ventricular event, it starts timer 34A which blanks amplifier 32 for the duration of its chosen refractory period. At the end of the time-out period for timer 34A, the blanking signal is removed from amplifier 32, returning it to its ready condition. At the same time, the removal of the blanking signal triggers atrial overlap timer 61 to begin its time period. The input out of timer 61 is designed to trigger on the trailing edge of the blanking signal from timer 34A, so that timer 61 begins its time period when timer 34A ends its time period.

The operation of the embodiment of FIG. 3 is similar to the operation of FIG. 1. Atrial sense amplifier 42 will enter its refractory period in response to either the sensing of an atrial event, or the sensing of a ventricular event. An atrial event sensed at lead 45 couples through gate 46 to switch flip-flop 60 to cause its output on conductor 48 to blank amplifier 42. Alternatively, a ventricular event causes a signal on conductor 35 that also couples through gate 46 to cause flip-flop 60 to blank amplifier 42. In either case, amplifier 42 remains refractory until the predetermined overlap time following the end of the refractory period of the ventricular sense amplifier. As amplifier 32 returns to its on condition following the time-out of timer 34A, atrial overlap timer 61 is triggered to provide the overlap time delay. This time delay may be approximately 30 ms, as was discussed above with reference to FIG. 2. At the end of the overlap period timer 61 sends a signal to flip-flop 60, switching it to remove the blanking signal from conductor 48 and return atrial sensing amplifier 42 to its on condition. The operation discussed above with respect to FIGS. 2A and 2B also applies to the operation of the embodiment of FIG. 3.

It will be seen from the foregoing that the present invention prevents delivery of an inappropriate or possibly dangerous stimulating pulse due to the occurrence of a PVC, by turning off the atrial sensing circuit upon occurrence of a ventricular event, and maintaining it off preferably until after, but in any event not prior to, the returning of the ventricular sensing amplifier to its on condition.

What is claimed:

1. A pacemaker for selectively delivering stimulating pulses to the heart in an atrial synchronous mode of operation, comprising:
   ventricular terminal means for connection to a patient's heart for delivering ventricular stimulation pulses thereto;
   generating means for selectively delivering ventricular electrical stimulation pulses to said ventricular terminal means;
   ventricular sense amplifier means connected to said ventricular terminal means for sensing ventricular beats of the heart, said ventricular sense amplifier means having a refractory period following the sensing of a ventricular heartbeat or stimulation pulse;
   atrial terminal means for connection to a patient's heart for sensing atrial beats;
   atrial sense amplifier means connected to said atrial terminal means for sensing atrial contractions of the heart;
   delay means operatively connected to said atrial sense amplifier means and said generating means for causing generation of a ventricular electrical stimulating pulse after a predetermined time interval following a sensed atrial contraction; and
   control means operatively connected to render said atrial sense amplifier means inoperative during the refractory period of said ventricular sensing amplifier.

2. A pacemaker according to claim 1 wherein said control means includes means for maintaining said atrial sensing amplifier inoperative during the refractory period of said ventricular sense amplifier and for a predetermined time interval thereafter.

3. A pacemaker according to claim 1 wherein said control means includes a blanking timer having a time-out interval not less than the length of the refractory period of said ventricular sense amplifier means, said blanking timer connected for rendering said atrial sense amplifier means inoperative during its time-out interval, and connected for starting its time-out interval on a sensed atrial or ventricular event.

4. A pacemaker according to claim 3 wherein the time-out interval of said blanking timer is greater than the length of the refractory period of the ventricular sense amplifier means, to provide an overlap for the refractory period of the atrial sense amplifer means.

5. A pacemaker according to claim 1 wherein said control means includes bistable switching means operatively connected for selectively rendering said atrial sense amplifier means inoperative upon occurrence of a sensed atrial or ventricular event, and including an atrial overlap timer operatively connected to provide an overlap time delay at the end of the refractory period of the ventricular sense amplifier means, and operatively connected to said bistable switching means to return said atrial sense amplifier means to its on condition at the end of said overlap time delay.

6. A pacemaker for selectively delivering stimulating pulses to the heart in an atrial synchronous mode of operation, comprising:

ventricular terminal means for connection to a patient's heart for delivering ventricular stimulation pulses thereto;
generating means for selectively delivering ventricular electrical stimulation pulses to said ventricular terminal means;
ventricular sense amplifier means connected to said ventricular terminal means for sensing ventricular beats of the heart;
atrial terminal means for connection to a patient's heart for sensing atrial beats;
atrial sense amplifier means connected to said atrial terminal means for sensing atrial contractions of the heart;
delay means operatively connected to said atrial sense amplifier means and said generating means for causing generation of a ventricular electrical stimulating pulse after a predetermined time interval following a sensed atrial contraction;
ventricular refractory period timer means operatively connected for rendering said ventricular sense amplifier means inoperative for a predetermined ventricular refractory period following a sensed ventricular event; and
atrial refractory period control means operatively connected for rendering said atrial sense amplifier means inoperative for an atrial refractory period beginning with a sensed atrial or ventricular event and continuing until after termination of said ventricular refractory period.

7. A control circuit for use in a heart pacemaker having an atrial terminal and a ventricular terminal, said circuit for selectively delivering stimulating pulses to the heart in an atrial synchronous mode of operation, comprising:
generating means for selectively delivering ventricular electrical stimulation pulses to said ventricular terminal;
ventricular sense amplifier means connected to said ventricular terminal means for sensing ventricular beats of the heart, said ventricular sense amplifier means having a refractory period following the sensing of the ventricular heartbeat or stimulation pulse;
atrial sense amplifier means connected to said atrial terminal for sensing atrial contractions of the heart;
delay means operatively connected to said atrial sense amplifier means and said generating means for causing generation of a ventricular electrical stimulating pulse after a predetermined time interval following a sensed atrial contraction; and
control means operatively connected to render said atrial sense amplifier means inoperative during a refractory period of said ventricular sensing amplifier.

8. A control circuit for use in a heart pacemaker having a ventricular terminal and an atrial terminal, said circuit for selectively delivering stimulation pulses to the heart in an atrial synchronous mode of operation, comprising:
generating means for selectively delivering ventricular electrical stimulation pulses to said ventricular terminal;
ventricular sense amplifier means connected to said ventricular terminal for sensing ventricular beats of the heart;
atrial sense amplifier means connected to said atrial terminal means for sensing atrial contractions of the heart;
delay means operatively connected to said atrial sense amplifier means and said generating means for causing generation of a ventricular electrical stimulation pulse after a predetermined time interval following a sensed atrial contraction;
ventricular refractory period timer means operatively connected for rendering said ventricular sense amplifier means inoperative for a predetermined ventricular refractory period following a sensed ventricular event and atrial refractory period control means operatively connected for rendering said atrial sense amplifier means inoperative for an atrial refractory period beginning with a sensed atrial or ventricular event and continuing until after termination of said ventricular refractory period.

* * * * *